US009643996B2

(12) United States Patent
Petrel et al.

(10) Patent No.: US 9,643,996 B2
(45) Date of Patent: May 9, 2017

(54) PROCESSES FOR PRODUCING PROTEIN MICROPARTICLES

(71) Applicant: BATTELLE MEMORIAL INSTITUTE, Columbus, OH (US)

(72) Inventors: Trevor Petrel, Columbus, OH (US); Craig Bartling, Lewis Center, OH (US); Lena Furci, Grove City, OH (US); Carrie Howland, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 14/356,367

(22) PCT Filed: Nov. 2, 2012

(86) PCT No.: PCT/US2012/063205
§ 371 (c)(1),
(2) Date: May 5, 2014

(87) PCT Pub. No.: WO2013/067281
PCT Pub. Date: May 10, 2013

(65) Prior Publication Data

US 2014/0288282 A1 Sep. 25, 2014

Related U.S. Application Data

(60) Provisional application No. 61/556,047, filed on Nov. 4, 2011.

(51) Int. Cl.
*A61K 45/00* (2006.01)
*A61L 33/12* (2006.01)
*C07K 1/113* (2006.01)
*A61K 9/16* (2006.01)

(52) U.S. Cl.
CPC .......... *C07K 1/1136* (2013.01); *A61K 9/1688* (2013.01)

(58) Field of Classification Search
None
See application file for complete search history.

(56) References Cited

U.S. PATENT DOCUMENTS

| | | | | |
|---|---|---|---|---|
| 6,051,256 | A * | 4/2000 | Platz | A61K 9/0075 424/46 |
| 2004/0219224 | A1* | 11/2004 | Yakovlevsky | A61K 9/1688 424/499 |
| 2007/0065372 | A1 | 3/2007 | Price et al. | |
| 2007/0258960 | A1* | 11/2007 | DeAngelo | A01N 1/02 424/93.7 |
| 2010/0166874 | A1 | 7/2010 | Malakhov et al. | |

OTHER PUBLICATIONS

Ye et al. Issues in long-term protein delivery using biodegradable microparticles, Journal of Controlled Release, 2010, Vo1.146, pp. 241-260.*

Ye et al., "Issues in long-term protein delivery using biodegradable microparticles", Journal of Controlled Release, 2010, vol. 146, pp. 241-260.

Supplementary EP Search Report issued Mar. 26, 2015 in EP12845924.5.

Bowen, P., "Particle Size Distribution Measurement from Millimeters to Nanometers and from Rods to Platelets", Journal of Dispersion Science and Technology, Taylor and Francis Group, New York, New York, US, vol. 23, No. 5, Jan. 1, 2002.

International Preliminary Report on Patentability issued on May 6, 2014 in PCT/US20121063205.

Communication pursuant to to Article 94(3) mailed by the EPO on Feb. 27, 2017 in EP Application. No. 12 845 924.5 filed in the name of Battelle Memorial Institute.

Freitas, Sergio et al., "Flow-through ultrasonic emulsification combined with static micromixing for aseptic production of microspheres by solvent extraction", European Journal of Pharmaceutics and Biopharmaceutics 61 (2005) 181-187.

Freitas, Sergio et al, "Ultrasonic atomisation into reduced pressure atmosphere—envisaging aseptic spray-drying for microencapsulation" Journal of Controlled Release 95 (2004) 185-195.

* cited by examiner

*Primary Examiner* — Jeanette Lieb

(74) *Attorney, Agent, or Firm* — Frank Rosenberg; C. Michael Gegenheimer

(57) ABSTRACT

Processes and apparatuses for producing biologically-active, protein-rich microparticles under ambient conditions are disclosed. A protein solution is atomized and collected in a dehydration solvent that is being mixed. The resulting protein microparticles retain high specific activity without the need for large amounts of stabilizing excipients.

22 Claims, 7 Drawing Sheets

PROCESSES FOR PRODUCING PROTEIN MICROPARTICLES

This application is a national stage filing and claims the priority benefit of PCT/US12/063205 filed Nov. 2, 2012 and also claims priority to U.S. Provisional Patent Application Ser. No. 61/556,047, filed Nov. 4, 2011. The disclosure of the provisional application is hereby incorporated by reference in its entirety.

BACKGROUND

The present disclosure relates to processes and apparatuses for producing high-loading, biologically active microparticles under ambient conditions, as well as the microparticles produced thereby. Such microparticles are useful in many fields, including drug delivery, for delivering proteins, peptides, and other bioactive molecules.

The production of protein microparticles for the purpose of stabilization or to provide a convenient vehicle for an intended application has been the subject of much investigation in recent years. Traditional methods for producing protein microparticles include controlled precipitation, milling of lyophilized protein product, microemulsion techniques, and spray drying, which is perhaps the most widely employed method. Each traditional method is limited in its capacity to control particle design features (e.g. size, dispersity, morphology, density) and most impart processing stresses that can lead to protein destabilization. For example, the standard approaches of spray drying and freeze drying impart considerable biological activity losses due to thermal, interfacial, and shear stress. Maintenance of biological activity and control of particle physical features during formation is critical in many fields of use, including but not limited to drug delivery. Process stress is typically mitigated by the addition of excess equivalents of stabilizing excipients (e.g. polyols, surfactants), which results in low microparticle biological density and creates an opportunity for off-target effects due to the added excipients. It would be desirable to be able to produce biologically-active, protein-rich microparticles for maximizing biological payload in fixed volume operations, such as drug delivery by injection.

BRIEF DESCRIPTION

The present disclosure relates to processes and apparatuses for producing microparticles that contain a high loading of bioactive macromolecules, such as proteins. Also included are the specific microparticles produced thereby. Briefly, the processes combine atomization with solvent-assisted dehydration to obtain solid particles that retain the biological activity of the payload and the physical characteristics of the original liquid droplets.

Disclosed in embodiments is a process for producing protein microparticles. A protein solution containing a protein and a liquid is atomized to form liquid droplets. The droplets are then collected in a mixed dehydration solvent to generate the protein microparticles.

The process may further comprise isolating the protein microparticles by: separating the microparticles from the dehydration solvent; extracting the microparticles into a secondary solvent; and evaporating the secondary solvent to obtain the protein microparticles. The secondary solvent may be evaporated under an inert gas.

In further embodiments, the protein in the microparticles may retain at least 90% of its original specific activity. In some embodiments, at least 85% of the microparticles have a diameter of 30 µm or less. In still others, the microparticles contain at least 75% by weight of the protein.

The protein solution may be atomized using an ultrasonic flow-through transducer. The liquid droplets produced by atomization can have an average droplet size of from about 0.5 µm to about 300 µm.

The protein microparticles may have an average size of from about 0.5 µm to about 300 µm.

The dehydration solvent may be partially soluble with the liquid in the protein solution. In some embodiments, the dehydration solvent has a water solubility capacity from about 1 to about 50 wt %.

The dehydration solvent may be a linear or branched aliphatic alcohol or an aromatic alcohol. In desirable embodiments, the dehydration solvent is n-decanol.

The protein solution and the dehydration solvent may independently have a maximum temperature of 40 degrees Celsius. In other embodiments, the protein solution and the dehydration solvent are at ambient temperature.

The volume ratio of the dehydration solvent to the protein solution may be at least 40:1.

The dehydration solvent may be mixed by vortexing or a method that introduces sustained turbulence throughout the dehydration solvent. The protein solution may be atomized at a flow rate of from about 0.2 mL/min to about 1 mL/min.

In specific embodiments, the resulting protein microparticles retain at least 90% of their original specific activity; at least 85% of the microparticles have a diameter of 30 µm or less; and the microparticles contain at least 75% by weight of the protein.

Also disclosed is an apparatus for producing protein microparticles, comprising: a reservoir for a protein solution; an atomizer; a collection vessel for collecting droplets produced by the atomizer; and a mixing device for mixing solvent in the collection vessel.

The atomizer may be an ultrasonic flow-through transducer. The mixing device may be a vortexer, an inverter, a paddle mixer, a stir bar mixer, or an ultrasonic transducer.

In some embodiments, the collection vessel is located so that a surface of a solvent in the collection vessel is from about 1 cm to about 4 cm below a nozzle of the atomizer.

Also disclosed are the protein microparticle(s) produced by the processes described herein.

Also disclosed is a composition containing protein microparticles, wherein the protein microparticles retain at least 90% of their original specific activity; wherein at least 85% of the microparticles have a diameter of 30 µm or less; and wherein the microparticles contain at least 75% protein by weight.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
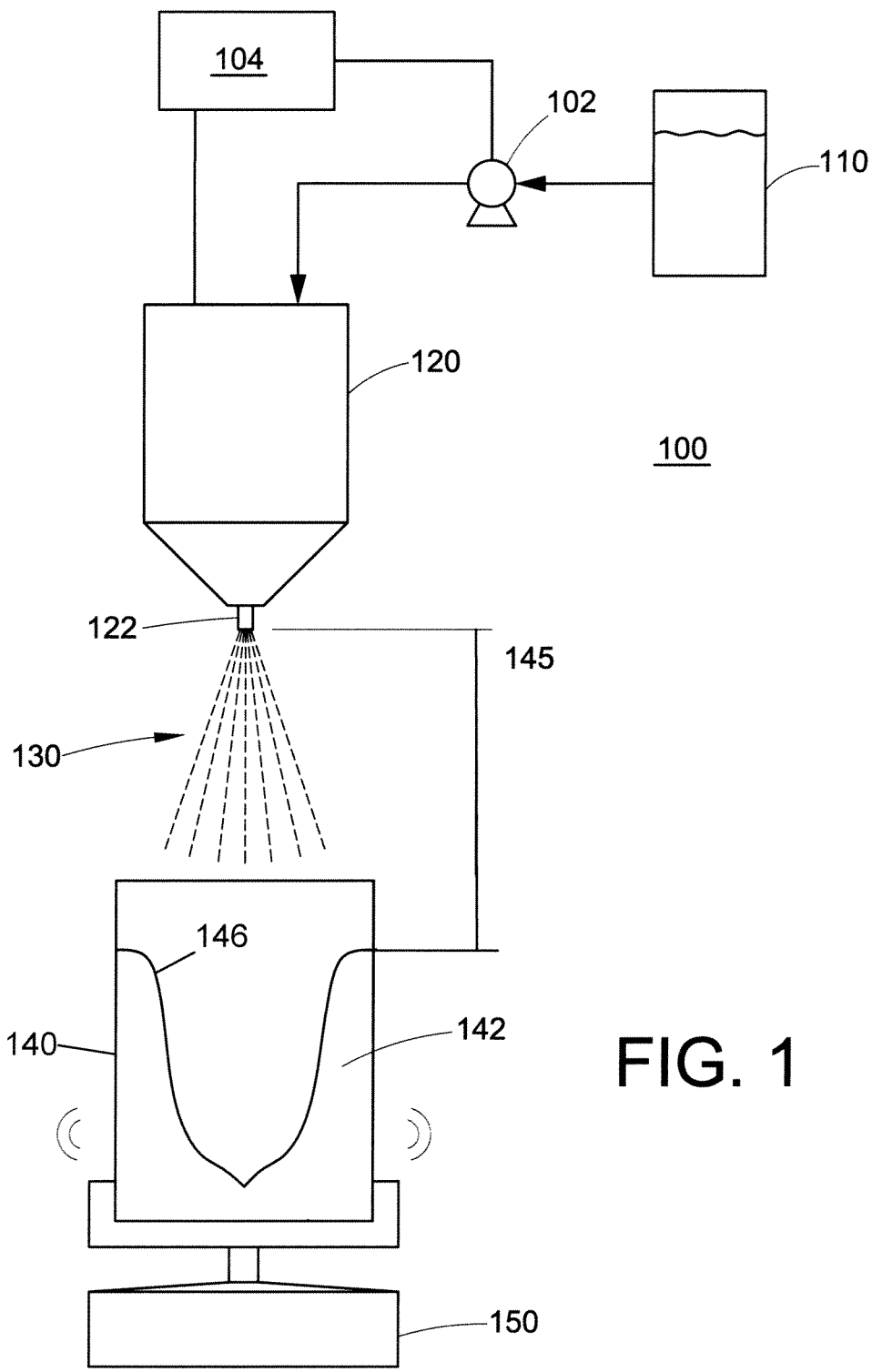
FIG. 1 is a schematic diagram describing an apparatus that can be used to practice the processes of the present disclosure.

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the following specification and the claims which follow, reference will be made to a number of terms which shall be defined to have the following meanings.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

The term "ambient temperature" refers to a temperature from 20° C. to 25° C.

The term "microparticles" refers to particles having a diameter of 1000 micrometers (μm) or less. In particular, the term "microparticles" is intended to include nanoparticles, which are particles having a diameter ranging from 1 nanometer to 1000 nanometers. The microparticles will be referred to in this disclosure as being spherical, though perfect sphericity is not required and other shapes are acceptable.

The processes of the present disclosure may be used to produce high-loading (i.e. minimal added excipient) protein microparticles without significant impact on the biological activity of the finished product. Put another way, the protein in the microparticles retain a high percentage of their original specific activity. The processes of the present disclosure may further be used to influence the gross morphology and internal features of the resultant microparticles.

Generally, the processes comprise atomizing a protein solution to form liquid droplets. The liquid droplets are then collected in a vessel that contains a dehydration solvent. Significantly, the dehydration solvent is mixed, or in other words is agitated, to generate the protein microparticles. This processing methodology and the reaction conditions are scalable between small batches and large-volume continuous manufacturing conditions.

Initially, a protein solution is formed. The protein solution includes a protein and a liquid. The term "protein" refers to a sequence of amino acids that is of sufficient chain length to produce a tertiary or quaternary structure. Examples of proteins include monoclonal antibodies, insulin, human growth hormone, and erythropoietin. The liquid is used as a vehicle to allow the protein to be shaped into a particle form. For example, the liquid can be water or any other aqueous vehicle known to solubilize protein and known to partition into organic solvent. In this regard, a "solution" is usually understood to refer to a mixture composed of only one phase. However, in the present disclosure the protein can be dissolved, emulsified, suspended, dispersed, or otherwise combined with the liquid to form the protein solution. The term "protein solution" is used here only for nomenclature purposes. The protein solution can be prepared at ambient temperatures and at any pH and/or ionic strength that will benefit the process.

The protein solution is then atomized to form liquid droplets. Such atomization techniques are frequently used in established protein processing methods such as spray drying. Liquid atomization of aqueous protein solutions has been demonstrated to produce highly monodisperse liquid droplets. Liquid droplets can also be generated rapidly and in large quantity through liquid atomization. The droplet size produced through atomization can be adjusted by varying the atomization conditions. In embodiments, the liquid droplets produced by atomization of the protein solution have an average droplet size of from about 0.5 µm to about 300 µm. The size of the droplets is also very uniform. In embodiments, the droplets should display a low polydispersity index (w), where w<0.3. Polydispersity index is a measure of the spread of droplet size distribution. For monodisperse aerosols, w=0 and reasonably monodisperse aerosols may be defined as w<0.3. During the atomization, the protein solution is not heated, or in other words is atomized at ambient temperatures.

In desirable embodiments, an ultrasonic flow-through transducer is used for the atomization. Briefly, this ultrasonic transducer operates by vibrating a nozzle at high speed. The vibrations pulverize liquid flowing through the nozzle into microdroplets. In this regard, the droplet size can be controlled by controlling the frequency at which the nozzle vibrates. For example, the vibration frequency of the ultrasonic transducer may be from about 25 kHz to about 120 kHz. The ultrasonic transducer can produce from about $10^7$ to about $10^{10}$ droplets per minute, assuming a median droplet size of 35 micrometers and a flow rate of 0.3 to 300 mL/min. The efficacy of the ultrasonic nozzle can be affected by its material, diameter, the vibration frequency, and other factors. For example, ceramic nozzles can have a larger diameter compared to metal nozzles at the same vibration frequency and thus obtain a higher flow rate.

The liquid droplets formed by the atomization are then collected in a mixed dehydration solvent. The dehydration solvent dehydrates the protein by absorbing the water, resulting in the generation of protein microparticles. This is also known as solvent-assisted dehydration. For efficient dehydration without compromising the properties of the protein in the liquid droplets, the dehydrating solvent should be capable of forming an interface with the liquid in the protein solution. In particular embodiments, the dehydration solvent should be partially soluble with water, so that the liquid droplets can be efficiently dehydrated without significant influx of solvent into the protein microparticles or mixing of the interface. In preferred embodiments, the dehydration solvent is a branched or linear aliphatic alcohol containing from 4 to about 12 carbon atoms or an aromatic alcohol containing from 6 to about 12 carbon atoms. The aromatic alcohol may include aliphatic sidechains. In specific embodiments, the dehydration solvent is n-decanol, which has a water solubility capacity of 3.4 wt %. Put another way, 3.4 grams of water can be dissolved in 100 grams of n-decanol. An example of an aromatic alcohol having aliphatic sidechains is phenylethyl alcohol. In other general embodiments, the dehydration solvent has a water solubility capacity of from about 1 to about 50 wt %. In other methods of measurement, about 1 to about 50 grams of water can be dissolved in 100 grams of the dehydration solvent. Combinations of two or more solvents to obtain a desired water solubility capacity or rate of dehydration are also contemplated. The dehydration solvent may have a lower density than the liquid in the protein solution to ensure adequate envelopment and mixing of the aqueous protein solution droplets with the dehydration solvent. In embodiments, the dehydration solvent has a density of about 0.500 to 0.999 g/mL. The dehydration solvent is held at a temperature contemplated to be optimal for the desired rate of dehydration and should be at least above the freezing point of both the protein solution and the dehydration solvent. The dehydration solvent, in some embodiments, has a maximum temperature of about 40 degrees Celsius. Put another way, the temperature of the dehydration solvent may be different from the temperature of the protein solution when the protein solution is being atomized. In some embodiments, the dehydration solvent is also at ambient temperature.

In other embodiments, the rate of solvent dehydration may be modulated by varying parameters such as temperature, mix condition, solvent composition, protein solution composition, or spray nozzle geometry to yield microparticles of desirable morphology for the purposes of, but not limited to, controlling the dissolution rate, particle density, or improving payload stability of the resulting microparticles. Stabilizing excipients known in the art may also be included in either the protein solution or the dehydration solvent to afford further desirable properties in the resultant microparticles.

The dehydration solvent is mixed or agitated during the collection of the liquid droplets containing the protein. This prevents the loss of the protein's specific activity. The dehydration solvent can be mixed using many different methods and apparatuses known in the art. For example, the dehydration solvent can be vortexed using a vortexer, inverted using an inverter, stirred using a paddle mixer or a stir bar mixer, or mixed using an ultrasonic transducer. In specific embodiments, the dehydration solvent is vortexed. Desirably, the mixing is done using a method that introduces sustained turbulence throughout the liquid volume of the dehydration solvent. The mixing may occur with or without disturbances, such as wave action and liquid sheet break-up, at the air:liquid interface. As another example, the dehydration solvent can be stirred in a collection vessel that is equipped with design features sufficient to induce turbulent flow.

The volume ratio of the dehydration solvent to the protein solution is, in embodiments, at least 40:1, to ensure the water solubility capacity of the dehydration solvent is not exceeded. In other embodiments, the protein solution is atomized at a flow rate of from about 0.2 milliliters per minute (mL/min) to about 1 mL/min.

The protein microparticles are then separated from the dehydration solvent. This separation can be achieved by any partitioning method known in the art, such as centrifugation, filtration, dialysis, or size-exclusion chromatography, to separate the microparticles from the bulk of the dehydration solvent. Any residual solvent can be removed by extraction of the microparticles into a secondary solvent, such as ethanol, pentanes, hexanes, ethers, chlorocarbons, ethylacetate, fluorocarbons, isopropanol, or tetrahydrofuran (THF). Generally, a suitable secondary solvent is one with high vapor pressure and in which the protein has poor solubility. The secondary solvent can then be evaporated to obtain the protein microparticles. If the secondary solvent is flammable, the evaporation can be carried out under an inert gas, such as neon, argon, or nitrogen ($N_2$).

The resulting protein microparticles contain a large amount of protein. In embodiments, the microparticles contain at least 75% by weight of the protein. In other embodiments, the protein in the microparticles retains at least 90% of its original specific activity.

The protein microparticles have an average particle size of from about 0.5 µm to about 300 µm, paralleling the sizes of the liquid droplets after atomization. In embodiments, at least 85% of the microparticles have a diameter of 30 µm or less.

In specific embodiments, the resulting protein microparticles retain at least 90% of their original specific activity; at least 85% of the microparticles have a diameter of 30 µm or less; and the microparticles contain at least 75% by weight of the protein.

One advantage of the processes of the present disclosure is that the size of the dry protein microparticles can be controlled by modification of the spray nozzle geometry during atomization, flow rate during atomization, changing the ultrasonic energy used during atomization, changing the composition of the protein solution, or and/or varying the composition of the dehydration solvent. These processes provide rapid and abundant formation of protein-rich, high density, spheroid protein microparticles.

It should be noted that standard methods like spray drying or freeze drying impart considerable processing stresses (e.g. thermal, interfacial, shear) that typically cause much of the biological activity in the protein to be lost. The addition of high-concentration stabilizing excipients can buffer against such processing stresses, but this results in particles with low protein density and reduced specific activity. Exemplary excipients include various polyols, such as trehalose or sucrose at 35 wt %, that have been described to stabilize through mechanisms of preferential protein hydration and surfactants, such as polysorbates at 0.1% that have been described to reduce protein aggregation and interfacial adsorption losses. In the present disclosure, no such excipients are needed, or such excipients can be used in smaller amounts. The mild atomization conditions, coupled with the rapid dehydration, result in protein microparticles that still have high biological specific activity without the need for the excipients.

In this regard, it appears the successful maintenance or recovery of biological activity from the processes of the present disclosure depends partially on the rate of droplet dehydration, which depends on efficient penetration of the solvent interface to overcome droplet coalescence and concurrent net air:liquid interfacial stress. It is believed that the mixing/vortexing prevents droplet coalescence during dehydration, increasing the rate of protein dehydration. Generally, it is believed that a higher rate of dehydration more effectively preserves specific activity (though a plateau may be reached).

There are several ways to change the rate of dehydration, including: (1) altering the water solubility capacity of the dehydration solvent in the collection vessel; (2) altering the protein concentration of the atomized liquid droplets; (3) altering the ionic strength of the atomized liquid droplets; (4) using different mixing technologies in the dehydration solvent vessel; (5) controlling the surface tension and viscosity of both the atomized liquid droplets and the dehydration solvent; (6) altering the droplet size or size distribution of the atomized plume through modulation of spray nozzle parameters or mixing parameters; (7) altering the impact velocity of the atomized liquid droplets at the solvent interface (in the dehydration solvent vessel); and/or (8) changing the process temperature;

The ionic strength of the atomized liquid droplets can be changed by adding ionizable salts such as KCl or NaCl at 10 to 500 mM, ionic detergents such as stearic acid at 0.5 to 5 wt %, or charged polymers such as polyacrylic acid at 0.002 to 2.0 wt % to the protein solution prior to atomizing.

The surface tension and viscosity of the protein solution (and the resulting atomized liquid droplets) or the dehydration solvent can be changed by adding surfactants to the appropriate liquid. Exemplary surfactants include poloxamers, polysorbates, betaines, and stearates. The surfactants may be used at a concentration below their determined or estimated respective critical micelle concentration (cmc) and are typically in the range of 0.001 to 1.0 wt %.

The impact velocity of the atomized liquid droplets upon the dehydration solvent can be changed by changing the distance between the atomizer and the dehydration solvent, or by altering the flow rate of the protein solution through the atomizer.

FIG. 1 is a schematic diagram illustrating a suitable apparatus 100 for practicing the processes of the present disclosure. The apparatus includes a reservoir 110, from which the protein solution is fed into the atomizer 120. As previously stated, the atomizer can be an ultrasonic flow-through transducer. The atomizer 120 has a nozzle 122, from which the liquid droplets 130 are dispensed. A collection vessel 140 is located below the atomizer for collecting the liquid droplets. A mixing device 150 is present to mix the dehydration solvent 142 in the collection vessel 140. The mixing device here is depicted as a vortexer which is external to the collection vessel. In particular embodiments, the collection vessel 140 is located so that the surface 146 of the dehydration solvent 142 is located a distance 145 of from about 1 cm to about 4 cm below the nozzle of the atomizer; this distance may be adjustable.

A fluid pump 102 can be used to deliver the aqueous protein solution containing the biological payload to the atomizer 120. A power source 104 is used to provide energy to the pump 102 and generate the ultrasonic pulse that atomizes the protein solution.

The processes of the present disclosure are amenable to scale-up since many protein liquid droplets are formed continuously, and particle formation is limited only by the capacity to continuously mix the volume of dehydration solvent, which is a function of the solubility limit. No expensive materials, complex engineering, or specialized infrastructure for manipulation of liquefied gases or other pressurized solvents needed. It is contemplated that the dehydration solvent can be recycled by use of automated liquid:liquid extraction, distillation, or other solid-phase drying techniques. Similarly, the processes can be made continuous, rather than requiring batch processes.

The protein microparticles made using the processes and devices described herein may be delivered using the core annular flow processes and devices described in U.S. Provisional Patent Application Ser. No. 61/556,491, filed on Nov. 7, 2011, and in U.S. Provisional Patent Application Ser. No. 61/673,864, filed on Jul. 20, 2012, the disclosures of which are hereby incorporated by reference in their entirety. They can also be used as part of the systems described in U.S. Provisional Patent Application Ser. No. 61/556,542, filed Nov. 4, 2011, or in the devices described in U.S. Provisional Patent Application Ser. No. 61/556,709, filed Nov. 4, 2011, the disclosures of which are hereby incorporated by reference in their entirety. They can also be dispensed using the chemical reaction systems and devices described in U.S. Provisional Patent Application Ser. No. 61/713,236, filed Oct. 12, 2012 or U.S. Provisional Patent Application Ser. No. 61/713,250, filed Oct. 12, 2012, the disclosures of which are hereby incorporated by reference in their entirety.

The following examples are for purposes of further illustrating the present disclosure. The examples are merely illustrative and are not intended to limit processes or devices made in accordance with the disclosure to the materials, conditions, or process parameters set forth therein.

Example 1

Figure 2:
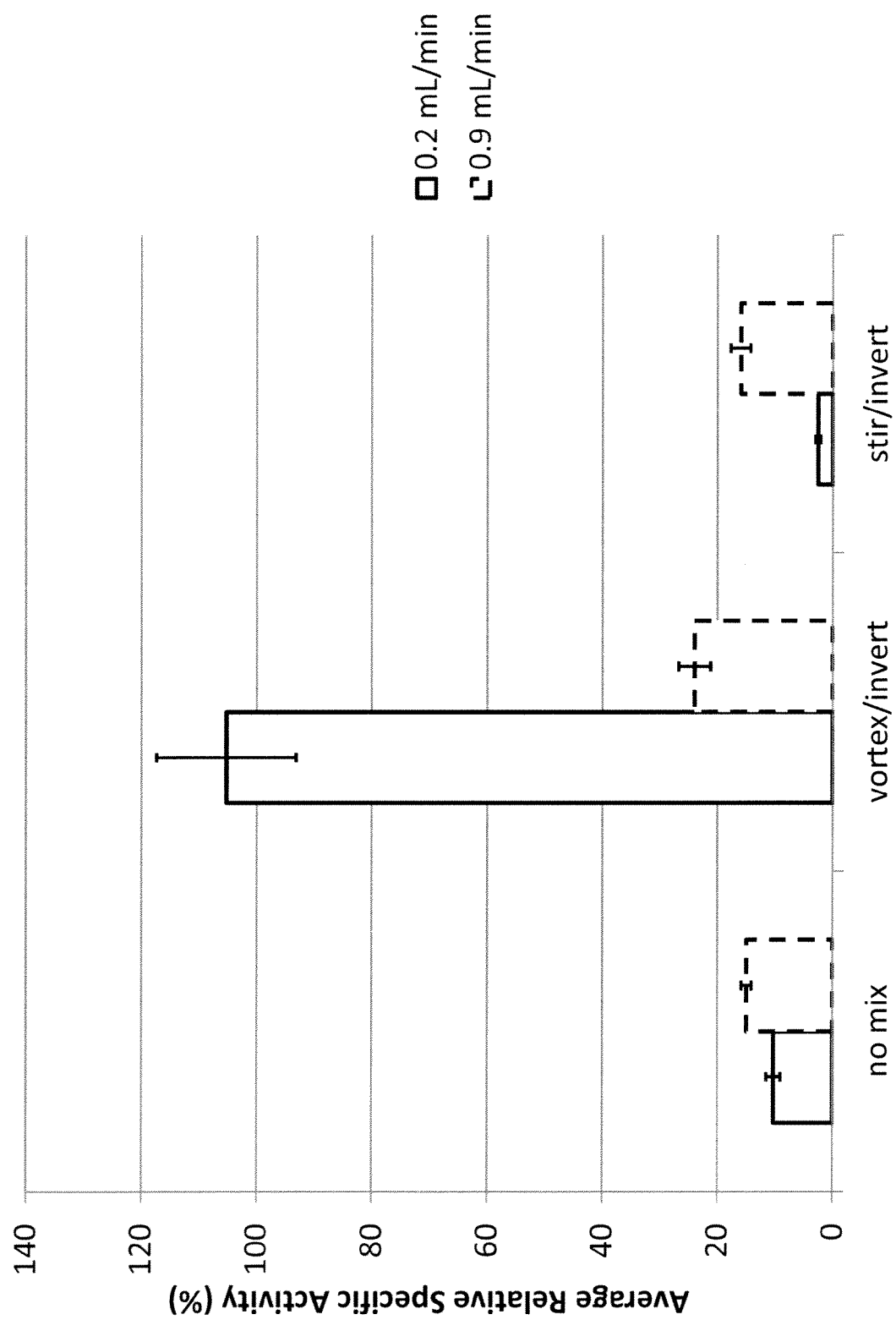
FIG. 2 is a graph showing the results of three different processing operations for forming protein microparticles.

The model enzyme glucose oxidase (GOx) was used to evaluate the potential to form biologically-active, protein-rich spheroid microparticles by ultrasonic spray delivery into a lower density, dehydrating solvent at room temperature. Three sets of different processing conditions are shown in FIG. 2. For each set of conditions, the GOx solution was sprayed at a flow rate of 0.2 mL/min or 0.9 mL/min. Average specific activity values were calculated as a percentage of specific activity recovered from an aliquot of the original GOx solution that was not subjected to atomization. GOx specific activity was determined by colorimetric detection of hydrogen peroxide in the presence of glucose normalized to the total protein concentration in the sample as determined by the bicinchoninic acid (BCA) method.

Atomization of a buffered GOx solution at a flow rate of 0.2 mL/min and 2.5 W input power using a 60 kHz commercial ultrasonic spray nozzle (Sono-tek) directly into n-decanol (not agitated) produced reasonably monodisperse spherical particles. The resulting median particle diameter, d(0.5), was 13 µm, with an associated span of 2.3. Particle span is defined as [d(0.9)–d(0.1)]/d(0.5) and is a measure of the width of the particle size distribution and is an estimate of population polydispersity. However, this process resulted in a near 90% loss of specific activity in the resulting protein microparticles, as assessed following buffer rehydration of the solid particle preparation. The same general result occurred at a flow rate of 0.9 mL/min. This is reflected in FIG. 2 in the "no mix" column.

Surprisingly, when the decanol reservoir was vortexed and combined with the identical atomization conditions, nearly 100% of the original GOX specific activity was retained. The optimal condition included atomized spray delivery into at least a forty-fold volume equivalent of anhydrous n-decanol positioned 1 to 2 cm below the ultrasonic spray nozzle outlet. The decanol reservoir was continuously mixed by low-speed vortex, followed by end-over-end inversion of the collected sample. The particles were subsequently isolated by centrifugation and solvent was removed by extraction into ethanol followed by evaporation under nitrogen gas. These results are seen in FIG. 2 in the "vortex/invert" column.

In the third set of conditions, the decanol reservoir was stirred using a magnetic stir bar instead of vortexed, followed by end-over-end inversion of the collected sample. The resulting particles had poor specific activity. These results are seen in FIG. 2 in the "stir/invert" column.

Figure 3:
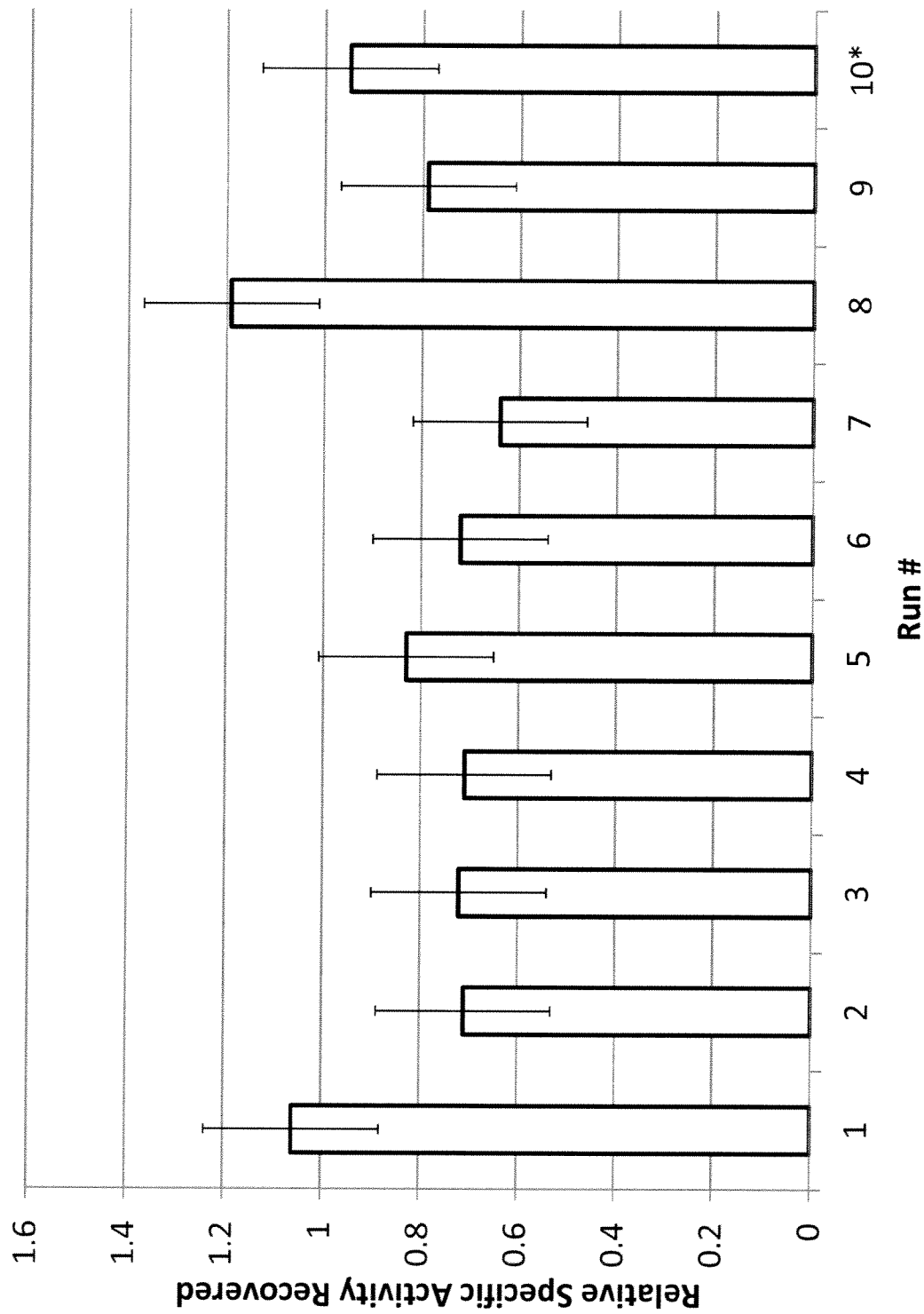
FIG. 3 is a graph showing the specific activity recovered for a model protein (GOx) from ten independent studies performed using processes of the present disclosure. Run #10 is displayed to indicate performance of the process when scaled 40-fold and mixed by complex stirring. Specific activity was determined by enzymatic and total protein analysis of recoverable GOx. Data shown indicates the average GOx specific activity recovered from each study relative to the specific activity of the prepared stock that did not undergo atomization or solvent-assisted drying. Each data set represents the average of three independent measurements (n=3) displayed to indicate the upper and lower bounds of the 95% confidence interval.

In a fourth set of conditions, the solvent reservoir was equipped with four opposing wall baffles and was mixed with counter-stirring at the top and bottom of the reservoir. Atomization of a buffered GOx solution at a flow rate of 0.2 mL/min and 2.5 W input power using a 60 kHz commercial ultrasonic spray nozzle (Sono-tek) directly into the mixed n-decanol produced microparticles similar to those obtained at smaller scale when mixed by vortex. Microparticles resulting from this process were found to retain significant biological activity, as seen in FIG. 3, which summarizes the results of 10 independent studies.

Figure 4:
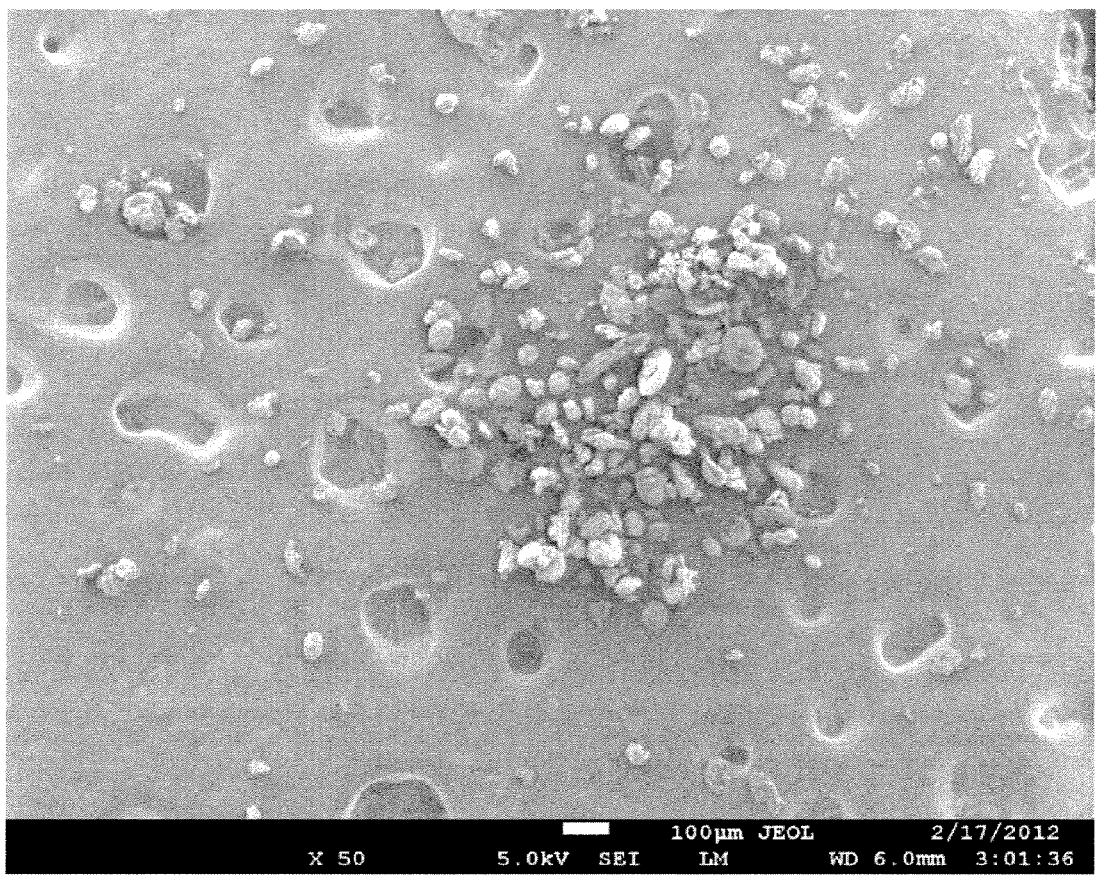
FIG. 4 is a scanning electron micrograph (SEM) of GOx microparticles recovered from Run #10 and showing the primary particle's spheroid morphology at 50× magnification.
Figure 5:
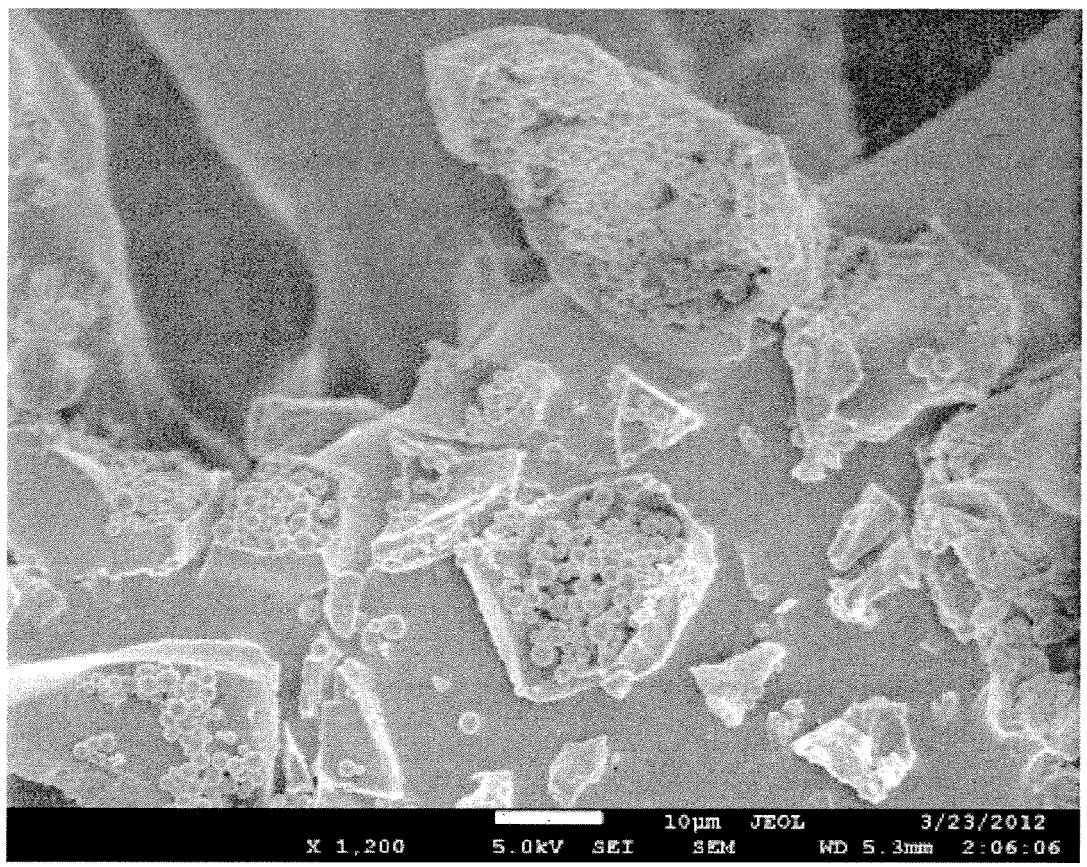
FIG. 5 is a scanning electron micrograph (SEM) of GOx microparticles recovered from Run #10 and showing the spheroid secondary particle payload following freeze fracture manipulation of the primary particles at 1200× magnification.
Figure 6:
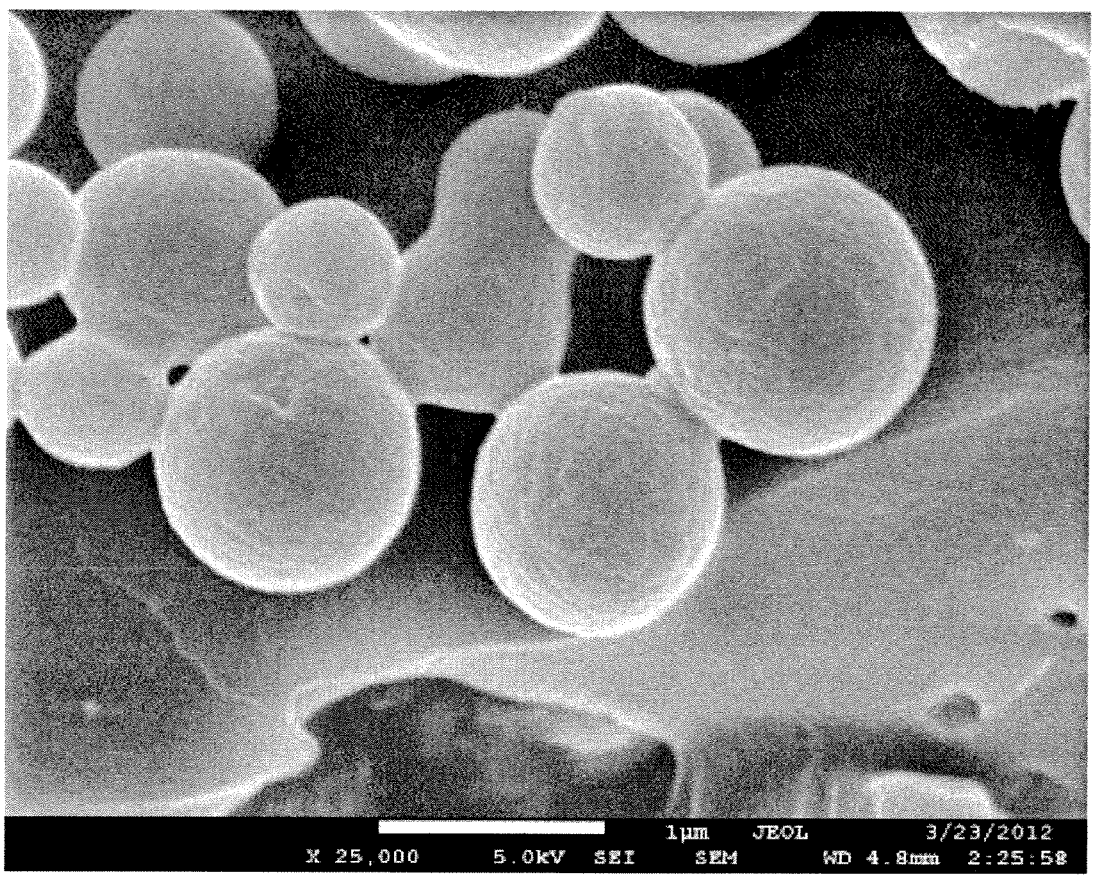
FIG. 6 is a scanning electron micrograph (SEM) of GOx microparticles recovered from Run #10 and showing the spheroid secondary particle payload following freeze fracture manipulation of the primary particles at 25,000× magnification.

Scanning electron micrographs were taken of GOx microparticles prepared at 40-fold scale. Samples were prepared by vacuum filtration of GOx microparticle ethanol suspensions over etched aluminum oxide (Anodisc, 0.02 µm pore size), followed by evaporative drying. Freeze fracturing of microparticles was accomplished by liquid nitrogen freezing of the sample between SEM imaging stands, followed by snap-separating the frozen imaging stands. This freeze fracture electron microscopy analysis revealed spheroid primary particles containing a spheroid secondary particle payload. FIG. 4 is a SEM showing the primary particles prior to freeze fracturing. FIG. 5 is a SEM showing the secondary particles at low magnification, and FIG. 6 is a SEM showing the secondary particles at high magnification.

Figure 7:
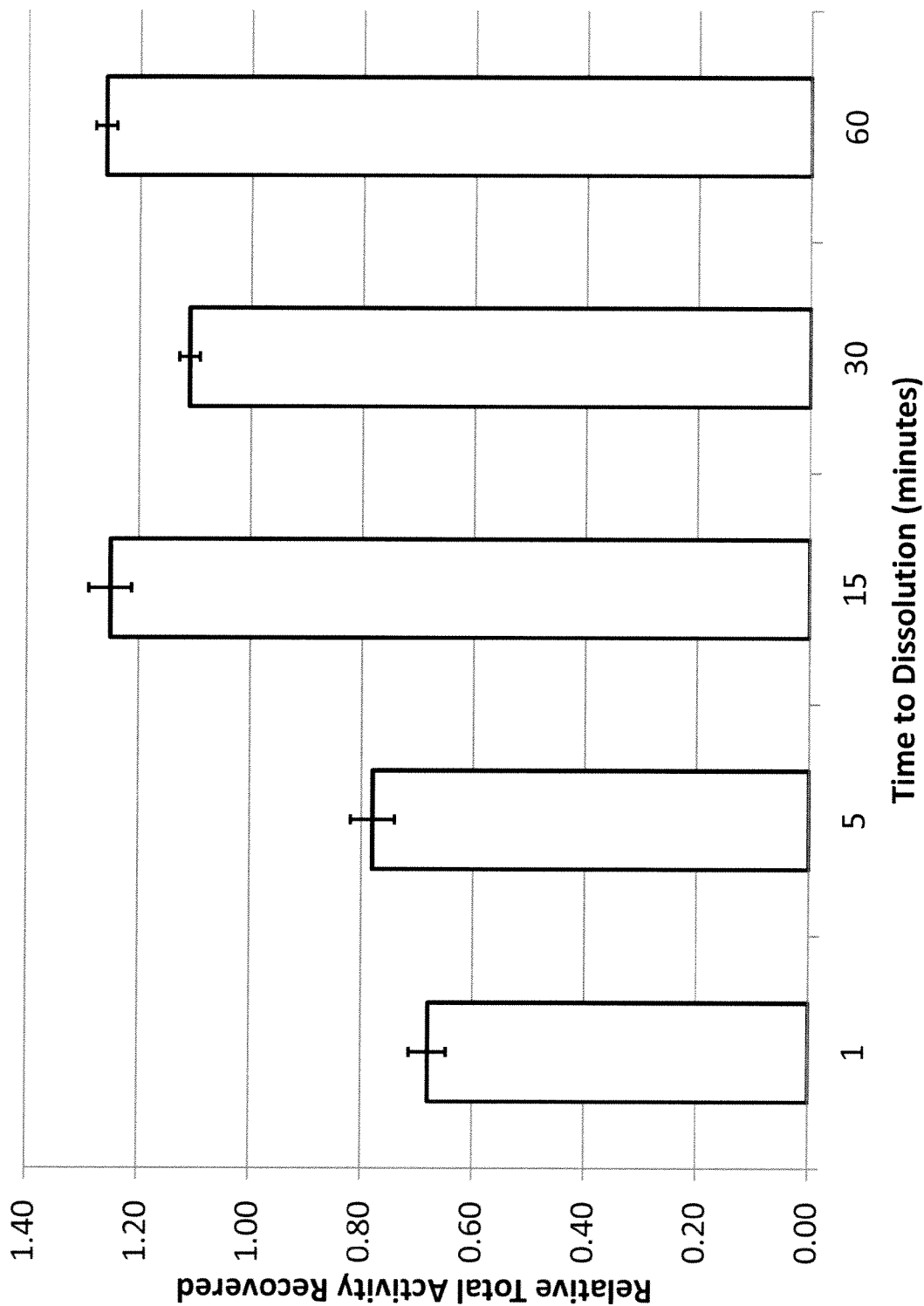
FIG. 7 is a graph showing the observed microparticle dissolution rate in 1×PBS, as determined by the analysis of total protein concentration in the supernatant of a centrifuged sample at each time point. Microparticles were found to completely dissolve within 15 minutes and recovered GOx retained near 100% specific activity. Each data set represents the average of three independent measurements (n=3) displayed to indicate the upper and lower bounds of the 95% confidence interval.

Microparticles resuspended in an aqueous vehicle, such as phosphate buffered saline (PBS), were found to fully dissolve within 15 minutes at room temperature and with periodic mixing. See FIG. 7.

Efficient recovery of GOx enzyme activity depended, in part, on the solution flow rate through the atomizing nozzle and mixing technology. Similar recoveries were noted for a second model protein payload, lysozyme (results not shown).

In contrast, when GOx was prepared by spray drying under standard conditions (400-800 linear feet per minute, lfpm) and 80° C. inlet temperature, buffered with a circulating low-temperature bath), only 30% of the original specific activity was recovered (results not shown). This compares poorly to the nearly 100% specific activity obtained in the present disclosure when turbulent mixing of the dehydration solvent was used to collect atomized liquid droplets of protein solution at a flow rate of 0.2 mL/min.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A process for producing protein microparticles, comprising:
    atomizing a protein solution containing a protein and a liquid to form liquid droplets;
    collecting the droplets in a mixed dehydration solvent to generate the protein microparticles; and
    further wherein mixing occurs with wave action and liquid sheet break-up at an air:liquid interface at the surface of the mixed dehydration solvent.

2. The process of claim 1, further comprising isolating the protein microparticles by:
    separating the microparticles from the dehydration solvent; extracting the microparticles into a secondary solvent; and
    evaporating the secondary solvent to obtain the protein microparticles.

3. The process of claim 2, wherein the secondary solvent is evaporated under an inert gas.

4. The process of claim 1 wherein the protein in the microparticles retains at least 90% of its original specific activity.

5. The process of claim 1, wherein at least 85% of the microparticles have a diameter of 30 µm or less.

6. The process of claim 1, wherein the microparticles contain at least 75% by weight of the protein.

7. The process of claim 1, wherein the protein solution is atomized using an ultrasonic flow-through transducer.

8. The process of claim 1, wherein the liquid droplets produced by atomization have an average droplet size of from about 0.5 µm to about 300 µm.

9. The process of claim 1, wherein the protein microparticles have an average size of from about 0.5 µm to about 300 µm.

10. The process of claim 1, wherein the liquid comprises water and wherein the dehydration solvent is partially soluble with the liquid in the protein solution; and wherein an interface forms with the dehydration solvent and the water in the liquid droplets so that the liquid droplets can be dehydrated without significant influx of solvent into the protein microparticles.

11. The process of claim 10, wherein the dehydration solvent has a water solubility capacity from about 1 to about 50 wt %.

12. The process of claim 10, wherein the dehydration solvent is a linear or branched aliphatic alcohol containing from 4 to 12 carbon atoms or an aromatic alcohol containing from 6 to 12 carbon atoms.

13. The process of claim 1, wherein the dehydration solvent is n-decanol.

14. The process of claim 1, wherein the protein solution and the dehydration solvent independently have a maximum temperature of 40 degrees Celsius.

15. The process of claim 1, wherein the protein solution and the dehydration solvent are at ambient temperature.

16. The process of claim 1, wherein the volume ratio of the dehydration solvent to the protein solution is at least 40:1.

17. The process of claim 1, wherein the dehydration solvent is mixed by vortexing or a method that introduces sustained turbulence throughout the dehydration solvent.

18. The process of claim 1, wherein the protein solution is atomized at a flow rate of from about 0.2 mL/min to about 1 mL/min.

19. The process of claim 1, wherein the resulting protein microparticles retain at least 90% of their original specific activity;
  wherein at least 85% of the microparticles have a diameter of 30 μm or less; and
  wherein the microparticles contain at least 75% by weight of the protein.

20. The process of claim 1, wherein the protein solution comprises an aqueous protein solution, wherein the liquid comprises water.

21. A process for producing protein microparticles, comprising:
  atomizing a protein solution containing a protein and a liquid to form liquid droplets;
  collecting the droplets in a mixed dehydration solvent to generate the protein microparticles;
  wherein the protein solution comprises an aqueous protein solution, wherein the liquid comprises water;
  and further wherein the dehydration solvent is in a collection vessel and a surface of the dehydration solvent is from about 1 cm to about 4 cm below a nozzle of an atomizer that atomizes the aqueous protein solution.

22. The process of claim 20, wherein the dehydration solvent is mixed by vortexing.

\* \* \* \* \*